US010512908B2

(12) United States Patent
Guy

(10) Patent No.: US 10,512,908 B2
(45) Date of Patent: Dec. 24, 2019

(54) METHOD FOR PREPARING A SAMPLE

(71) Applicant: BIOMÉRIEUX, Marcy-l'Etoile (FR)

(72) Inventor: Michel Guy, Grenoble (FR)

(73) Assignee: Biomerieux, Marcy-L'etoile (FR)

( * ) Notice: Subject to any disclaimer, the term of this patent is extended or adjusted under 35 U.S.C. 154(b) by 0 days.

(21) Appl. No.: 16/020,569

(22) Filed: Jun. 27, 2018

(65) Prior Publication Data

US 2018/0311660 A1 Nov. 1, 2018

Related U.S. Application Data

(62) Division of application No. 15/027,624, filed as application No. PCT/EP2014/072800 on Oct. 23, 2014, now Pat. No. 10,046,320.

(30) Foreign Application Priority Data

Oct. 23, 2013 (EP) .................................... 13306463

(51) Int. Cl.
*B01L 3/02* (2006.01)
*G01N 1/28* (2006.01)
*B01L 3/00* (2006.01)
*G01N 1/30* (2006.01)

(52) U.S. Cl.
CPC ......... *B01L 3/0217* (2013.01); *B01L 3/50825* (2013.01); *G01N 1/286* (2013.01); *G01N 1/30* (2013.01); *B01L 3/0275* (2013.01); *B01L 2200/025* (2013.01); *B01L 2200/026* (2013.01); *B01L 2300/042* (2013.01); *B01L 2300/046* (2013.01); *B01L 2300/0832* (2013.01)

(58) Field of Classification Search
None
See application file for complete search history.

(56) References Cited

U.S. PATENT DOCUMENTS

| 4,808,381 A * | 2/1989 | McGregor ............ A61J 1/1406 215/307 |
| 5,130,254 A | 7/1992 | Collier et al. |
| 5,314,825 A | 5/1994 | Weyrauch et al. |
| 6,575,205 B2 | 6/2003 | Epstein et al. |
| 9,360,493 B1 | 6/2016 | Seguin |
| 10,046,320 B2 * | 8/2018 | Guy ....................... G01N 1/286 |
| 2013/0065223 A1 | 3/2013 | Klein et al. |
| 2013/0092690 A1 | 4/2013 | Skakoon |
| 2015/0298120 A1 | 10/2015 | Westberg et al. |

FOREIGN PATENT DOCUMENTS

| EP | 0126390 A2 | 11/1984 |
| EP | 2545993 A1 | 1/2013 |
| WO | 9119181 A1 | 12/1991 |

OTHER PUBLICATIONS

Mai Le, "Pre-Treatment is key in GPP", Luminex, Feb. 19, 2013 (Feb. 19, 2013) Retrieved from the Internet: URL: http://www.luminexcorp.com/blog/pre-treatment-is-key-in-gpp/[retrieved on Mar. 6, 2014].

* cited by examiner

*Primary Examiner* — Ralph J Gitomer
(74) *Attorney, Agent, or Firm* — Drinker Biddle & Reath LLP

(57) ABSTRACT

A method for preparing a sample involves providing a container having an open end; a pipette for transferring material to and from the container; a cap to seal the open end and to allow the pipette to enter the container. The cap and pipette have cooperating stop portions for preventing the pipette from advancing where, upon engagement a pipette tip stops above a first predetermined level but below a second predetermined level. The method involves placing lysis facilitating means in the container at or below the first predetermined level; and a lysis buffer solution to cover the lysis facilitating means; sealing the open end; placing sample material with the pipette; subjecting the sample to lysis; inserting the pipette into the container until the cooperating stop portions and the pipette engage and the pipette tip stops approximately midway between the first and the second levels; and aspirating the obtained lysate.

8 Claims, 1 Drawing Sheet

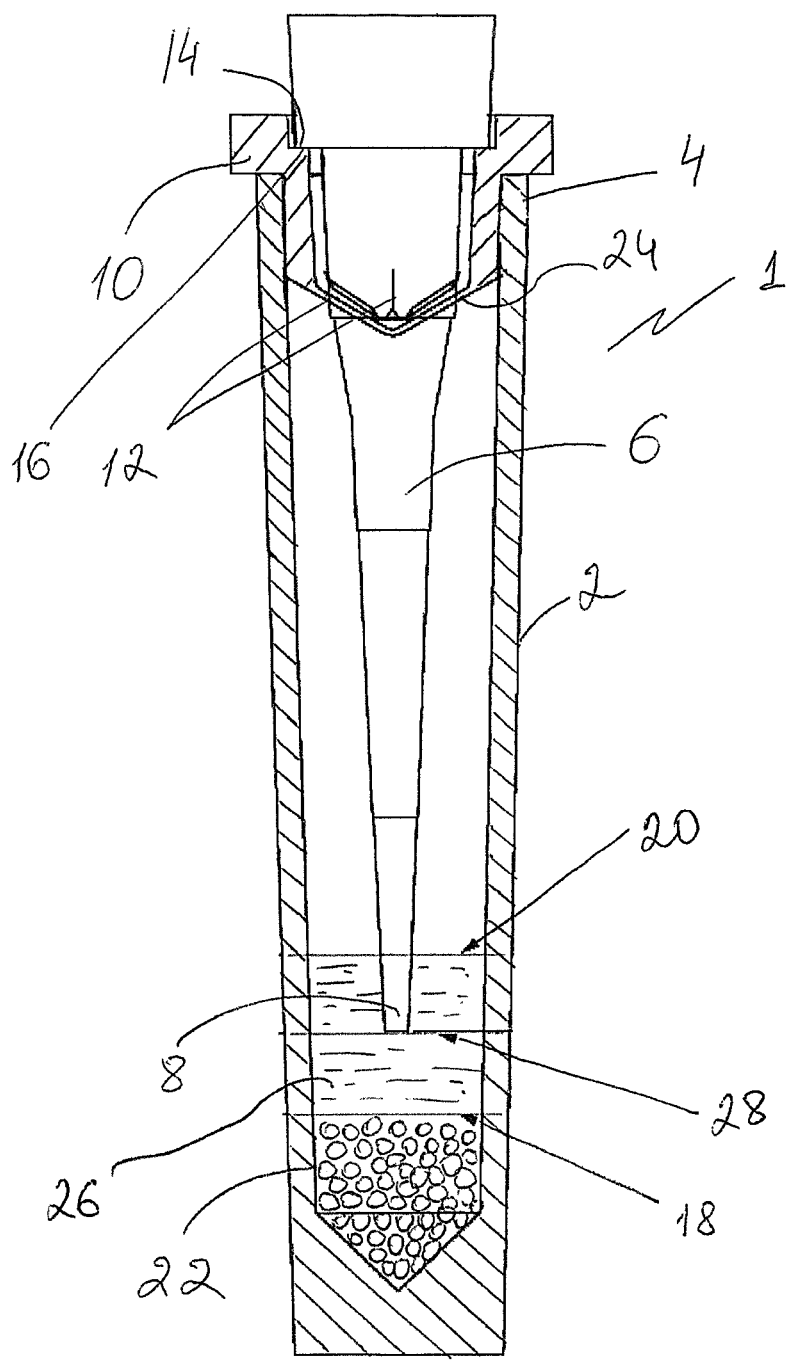

METHOD FOR PREPARING A SAMPLE

RELATED APPLICATION

This application is a divisional of U.S. patent application Ser. No. 15/027,624, filed on Apr. 6, 2016, the disclosure of which is incorporated herein by reference in its entirety.

FIELD OF THE INVENTION

The present invention provides a kit, a method and an assembly for preparing a sample, such as, for example, but not limited thereto, for preparing a sample of biological material for analysis.

BACKGROUND OF THE INVENTION

In the biotechnological industry, lysis kits are used to prepare biological material for analysis by turning the biological material into lysate. A lysis kit comprises a tube, a cap sealing the tube and a pipette tip for placing a sample of biological material into the tube and for withdrawing lysate from the tube. The tube may contain beads to help break the cells in the sample mechanically and to homogenise the disrupted cell material. The tube also contains a lysis buffer solution usually comprising a liquid reagent to help disintegrate the cells further without damaging the cell components to be analysed. The lysate is withdrawn from the tube by the pipette tip and transferred for analysis. The lysis kit has to satisfy a number of requirements which include:

- The cap has to seal securely the lysis tube containing the lysis buffer solution and the beads
- The pipette tip has to enter the lysis tube without the need to open the lysis tube or without the need to remove the cap
- Easy piercing of the cap since the operator can apply only a limited force and secondly due to the fragility of the pipette tip used
- The pipette tip should be easily removable from the lysis tube
- Evaporation of the lysis buffer solution must be limited
- The cap must provide good sealing during transportation/storage and during bead beating even if the cap has been pierced
- Biological cross contamination must be avoided even if the cap has been pierced
- The cap must be compatible with the pipette tip Also, the pipette tip has to be correctly positioned in the tube for dispensing the sample and to aspirate the lysate. Many solutions have been proposed so far to address the above requirements. However, a need still remains for improved pipette tip positioning in the tube in order to prevent undesired components of the lysate from entering the pipette during aspiration.

Accordingly, the object of the present invention is to provide a kit, a method and an assembly for preparing a sample of material which provide for improved pipette positioning in the tube compared to existing arrangements.

SUMMARY OF THE INVENTION

According to a first aspect of the invention, there is provided a kit for preparing a sample of material, the kit comprising
- a container having an open end;
- a pipette for transferring the material to and from the container, the pipette having an open tip for drawing and dispensing the material;
- a cap configured to seal the open end of the container and to allow the pipette tip enter the container through the cap
- the cap and the pipette comprising cooperating stop portions for preventing the pipette from advancing into the container upon engagement of the stop portions; wherein
- the pipette, the cap and the container are mutually configured such that upon engagement of the cooperating stop portions, the tip of the pipette stops above a first predetermined level but below a second predetermined level in the container;
- the first predetermined level being a level for a first substance;
- the second predetermined level being a level for a second substance, and
- the first level being lower than the second level.

At least the second substance may be a liquid. Preferably, the first and second substances are non-miscible. Preferably, the kit is a lysis kit for preparing a sample of biological material for analysis. Preferably, the first substance comprises a lysis facilitating means. The lysis facilitating means may comprise beads. Preferably, the second substance comprises a lysis buffer solution. Preferably, in use, the first substance is covered by the second substance in the container. Preferably, the first predetermined level is an upper level of the first substance and the second predetermined level is an upper level of the second substance.

Preferably, upon engagement of the cooperating stop portions the pipette tip is spaced by a predetermined distance above the first predetermined level.

Preferably, the pipette tip is positioned approximately midway between the first and the second levels.

The container may have a first level mark indicating the first predetermined level.

The container may have a second level mark indicating the second predetermined level.

Amounts of the first substance, the second substance and the material may fluctuate within respective predetermined ranges of allowed amounts.

The cap may define a slit for receiving the pipette tip. The cap is preferably elastically deformable for easy insertion and withdrawal of the pipette tip via the slit. The cap may be a silicone cap or a thermoplastic elastomer (TPE) cap. The slit is preferably self-sealable. Preferably, portions of the cap around the slit are configured to wipe the pipette tip upon withdrawal of the pipette tip from the container to prevent the material being aspirated from adhering to external surfaces of the pipette tip to prevent cross contamination.

Preferably, the cap is sized and shaped to withstand a pressure of about 0.2 MPa. The ability of the cap to withstand the pressure up to 0.2 MPa ensures airtightness and avoids accidental removal of the cap when the pipette tip is pulled out of the tube.

The container may be provided in the form of a tube.

The kit comprises instructions for using the kit to prepare a sample of material for analysis.

A plurality of kits is preferably provided in which the respective amounts of the first substance, the second substance and the sample material and the respective first predetermined levels are the same. Preferably, the second predetermined levels are the same in the plurality of kits.

According to a second aspect of the invention there is provided a method for preparing a sample of material, the method comprising the steps of:
  a) providing a container having an open end;
    a pipette for transferring the material to and from the container, the pipette having an open tip for drawing and dispensing the material;
    a cap for sealing the open end of the container, the cap being configured to allow the pipette tip enter the container through the cap
    the cap and the pipette tip comprising cooperating stop portions for preventing the pipette tip from advancing into the container upon engagement of the stop portions; wherein
    the pipette, the cap and the container are mutually configured such that upon engagement of the cooperating stop portions, the tip of the pipette stops above a first predetermined level but below a second predetermined level in the container;
    the first predetermined level being a level for a first substance in the container;
    the second predetermined level being a level for a second substance, and
    the first level being lower than the second level;
  b. placing a predetermined amount of the first substance in the container at or below the first predetermined level; and a predetermined amount of the second substance covering the first substance;
  c. sealing the open end of the container with the cap;
  d. inserting the pipette tip into the container through the cap until the cooperating stop portions of the cap and the pipette engage and the tip of the pipette stops above the first predetermined level; and
  e. aspirating the material.

Preferably, at least the second substance is a liquid. Preferably, the first and second substances are non-miscible. Preferably, the method involves preparing a sample of biological material for analysis by subjecting the sample to lysis. Preferably, the first substance comprises a lysis facilitating means. The lysis facilitating means may comprise beads. Preferably, the second substance comprises a lysis buffer solution. Preferably, the first predetermined level is an upper level of the first substance and the second predetermined level is an upper level of the second substance.

Preferably, prior to step d) the method includes the steps of:
  placing a predetermined amount of sample biological material into the second substance in the container; the resulting mixture covering the first substance and, preferably, an upper level of the mixture being disposed in the container at or above the second predetermined level; and
  subjecting the sample to lysis in the container.

Preferably, upon engagement of the cooperating stop portions the pipette tip is spaced by a predetermined distance above the first predetermined level.

Preferably, the pipette tip is positioned approximately midway between the first and the second levels.

The container may have a first level mark indicating the first predetermined level.

The container may have a second level mark indicating the second predetermined level.

The respective predetermined amounts of the first substance, the second substance and the material may fluctuate within respective predetermined ranges of allowed amounts.

The method includes repeating steps a)-d) to prepare a plurality of samples of material for analysis in a corresponding plurality of containers wherein the respective amounts of the first substance, the second substance and the sample material and the respective first predetermined levels are the same. Preferably, the second predetermined levels are the same.

According to a third aspect of the invention, there is provided an assembly for preparing a sample of material for analysis, the assembly comprising
  a container having an open end;
  a pipette for transferring the material to and from the container, the pipette having an open tip for drawing and dispensing the material;
  a cap sealing the open end of the container, the cap being configured to allow the pipette tip enter the container through the cap
  the cap and the pipette comprising cooperating stop portions for preventing the pipette from advancing into the container upon engagement of the stop portions; wherein
  the pipette, the cap and the container are mutually configured such that upon engagement of the cooperating stop portions, the tip of the pipette stops above a first predetermined level but below a second predetermined level in the container;
  the first predetermined level being a level for a first substance;
  the second predetermined level being a level for a second substance, and
  the first level being lower than the second level;
  wherein a predetermined amount of the first substance is disposed in the container at or below the first predetermined level; and
  wherein a predetermined amount of the second substance is disposed in the container covering the first substance.

Preferably, at least the second substance is a liquid. Preferably, the first and second substances are non-miscible. Preferably, the assembly is a lysis assembly for preparing a sample of biological material for analysis. Preferably, the first substance comprises a lysis facilitating means. The lysis facilitating means may comprise beads. Preferably, the second substance comprises a lysis buffer solution. Preferably, the first predetermined level is an upper level of the first substance and the second predetermined level is an upper level of the second substance.

Preferably, the second substance is disposed in the container together with a predetermined amount of sample biological material, the resulting mixture covering the first substance and, preferably, an upper level of the mixture being disposed in the container at or above the second predetermined level.

Preferably, upon engagement of the cooperating stop portions the pipette tip is spaced by a predetermined distance above the first predetermined level.

Preferably, the pipette tip is positioned approximately midway between the first and the second levels.

The container may have a first level mark indicating the first predetermined level.

The container may have a second level mark indicating the second predetermined level.

The respective predetermined amounts of the first substance, the second substance and the material may fluctuate within respective predetermined ranges of allowed amounts.

A plurality of assemblies is preferably provided in which the respective amounts of the first substance, the second substance and the sample material and the respective first predetermined levels and the second predetermined levels are the same in the plurality of assemblies.

Thus, in accordance with the present invention, the tip of the pipette is always automatically stopped at the same distance above an upper level of the first substance (located at the first predetermined level), thereby preventing human error and ensuring that the sample is collected from the correct part of the container so that no undesired material enters the pipette during aspiration.

It will be appreciated that although the present invention is beneficial in an application to lysis, other uses are indeed within the scope of the present invention in which a specific substance requires to be aspirated without aspirating another non-miscible substance from the same vessel.

All essential, preferred or optional features of any one of the first, second or third aspects of the present invention can be provided in conjunction with another of the first, second or third aspects of the present invention where appropriate.

DETAILED DESCRIPTION OF THE INVENTION

Embodiment of the present invention will now be described, by way of example only, with reference to the accompanying drawing in which:

FIG. 1 is a cross-sectional elevation of an assembly in accordance with the invention.

Referring to FIG. 1, a kit, a method and an assembly for preparing a sample in accordance with the present invention will be jointly described in use for preparing a sample of biological material for analysis through lysis.

As shown in FIG. 1, a lysis assembly (which may be assembled from a lysis kit provided by the present invention) of the present invention is indicated generally by reference numeral 1. The assembly 1 includes a container provided in the form of a tube 2 in the presently described embodiment. The tube 2 has an open end 4. The assembly 1 further comprises a pipette 6 for transferring biological material to and from the tube 2. The pipette 6 has an open tip 8 for drawing and dispensing the biological material.

A cap 10 seals the open end 4 of the tube 2. The cap 10 is configured to allow the pipette tip 8 enter the tube 2 through the cap 10. For this purpose, the cap 10 defines a self-sealable slit 12 for receiving the pipette tip 8. The cap 10 is preferably made from silicone or TPE to render the cap 10 elastically deformable for easy insertion and withdrawal of the pipette tip 8 via the slit 12. Portions of the cap 10 around the slit 12 wipe the pipette tip 8 upon withdrawal of the pipette tip 8 from the tube 2 to prevent sample biological material and lysate obtained in the tube 2 from adhering to external surfaces of the pipette tip 8 to prevent cross contamination. Additionally, the cap 10 is sized and shaped to withstand a pressure of about 0.2 MPa. Although the cap 10 in FIG. 1 is shown having a conical base 24, other configurations, such as a flat base with a slit, are within the scope of the present invention.

The cap 10 and the pipette 6 comprise cooperating stop portions provided by ledge faces 14, 16 of the pipette 6 and the cap 10, respectively, for preventing the pipette 6 from advancing into the tube 2 upon engagement of the ledge faces 14, 16. As shown in FIG. 1, upon engagement of the cooperating ledge faces 14, 16, the tip 8 of the pipette 6 stops above a first predetermined level 18 but below a second predetermined level 20 in the tube 2. The first predetermined level 18 is a level of lysis facilitating means provided in the form of beads 22 in the tube 2. The second level 20 above the first level 18 is a level of the resulting lysis buffer solution 26 in the tube 2. For convenience, although not shown in the drawing, the tube 2 may have a first level mark indicating the first predetermined level 18 and a second level mark indicating the second predetermined level 20.

In practice, a predetermined amount of a first substance in the form of lysis facilitating beads 22 is placed in the tube 2 at or below the first predetermined level 18 and a predetermined amount of a second substance in the form of lysis buffer solution is placed in the tube 2. The first and second substances are non-miscible. The open end 4 of the tube 2 is then sealed with the cap 10. A predetermined amount of sample biological material is then placed into the tube 2 by the pipette 6 which is inserted into the tube 2 through the slit 12 in the cap 10. The respective predetermined amounts of beads 22, lysis buffer solution 26 and sample biological material may fluctuate within respective predetermined ranges of allowed amounts. The upper level of the resulting solution in the tube 2 becomes disposed in the tube 2 at or above the second level 20. The sample is then subjected to lysis in the tube 2. In order to retrieve the obtained lysate from the tube 2, the pipette tip 8 is inserted into the tube 2 through the slit 12 in the cap 10 until the cooperating ledge faces 14, 16 of the pipette 6 and the cap 10, respectively, engage and the tip 8 of the pipette tip 6 stops at a level 28 approximately midway between the first and the second levels 18, 20 at a predetermined distance above the first predetermined level 18. The lysate is then aspirated and can be transferred to the analysis site. In this manner, the tip 8 of the pipette 6 is always automatically stopped at the same distance above the beads 22, thereby preventing human error and ensuring that the sample biological material and the lysate is collected from the correct part of the solution in the tube 2 and no undesired material enters the pipette 6 during aspiration.

The above steps are repeated with a plurality of assemblies 1 to prepare a plurality of samples of biological material for analysis and the respective amounts of beads 22, lysis buffer solution 26 and sample biological material while the respective first predetermined levels 18 and second predetermined levels 20 are maintained the same across the plurality of assemblies 1.

It will be appreciated that although a preferred embodiment of the present invention has been described in an application to lysis, other uses are indeed within the scope of the present invention in which a specific substance requires to be aspirated from a vessel containing at least two non-miscible substances without aspirating the second substance from the same vessel.

Whilst specific embodiments of the present invention have been described above, it will be appreciated that modifications are possible within the scope of the present invention as defined in the appended claims.

The invention claimed is:

1. A method for preparing a sample of biological material for analysis, the method comprising the steps of:
   a) providing a kit comprising a container having an open end;
      a pipette for transferring the biological material to and from the container, the pipette having an open tip for drawing and dispensing the biological material;
      an airtight cap for sealing the open end of the container in an airtight manner, the cap being configured to allow the pipette tip to enter the container through the cap
      the cap and the pipette tip comprising cooperating stop portions for preventing the pipette tip from advancing into the container upon engagement of the stop portions; wherein the pipette, the cap and the container are mutually configured such that upon engagement of the cooperating stop portions, the tip of the pipette stops above a first predetermined level but below a second predetermined level in the container, approximately midway between the first and the second levels;

the first predetermined level being a level for lysis facilitating means;

the second predetermined level being a level for lysis buffer solution, and the first level being lower than the second level;

b) placing a predetermined amount of lysis facilitating means in the container at or below the first predetermined level; and a predetermined amount of lysis buffer solution so that the lysis buffer solution covers the lysis facilitating means;

c) sealing the open end of the container in an airtight manner with the cap;

d) placing a predetermined amount of sample biological material into the container, the resulting mixture being disposed in the container at or above the second predetermined level;

e) subjecting the sample to lysis in the container;

f) inserting the pipette tip into the container through the cap until the cooperating stop portions of the cap and the pipette engage and the tip of the pipette stops above the first predetermined level approximately midway between the first and the second levels; and g) aspirating the obtained lysate.

2. A method as claimed in claim 1, wherein upon engagement of the cooperating stop portions the pipette tip is spaced by a predetermined distance above the first predetermined level.

3. A method as claimed in claim 1, wherein the container has a first level mark indicating the first predetermined level.

4. A method as claimed in claim 3, wherein the container has a second level mark indicating the second predetermined level.

5. A method as claimed claim 1, wherein the cap defines a slit for receiving the pipette tip, the method comprising elastically deforming the cap during insertion and withdrawal of the pipette tip via the slit and allowing the slit to self-seal upon withdrawal of the pipette.

6. A method as claimed in claim 5, the method comprising allowing portions of the cap around the slit to wipe the pipette tip during withdrawal of the pipette tip from the container to prevent the material being aspirated from adhering to external surfaces of the pipette tip to prevent cross contamination.

7. A method as claimed in claim 1, the method comprising providing a plurality of said kits in which the respective amounts of lysis facilitating means, lysis buffer solution and sample of biological material are the same and the respective first predetermined levels and the second predetermined levels in the container are the same.

8. A method as claimed in claim 1, wherein the lysis facilitating means comprises beads.

* * * * *